United States Patent [19]

Sou

[11] Patent Number: 5,318,505

[45] Date of Patent: Jun. 7, 1994

[54] MEDICAL BELT

[76] Inventor: Toshio Sou, 40-15, Nakano 5-Chome, Nakano-Ku, Tokyo, Japan

[21] Appl. No.: 895,138

[22] Filed: Jun. 8, 1992

[51] Int. Cl.[5] .......................... A61F 5/00; A61F 5/03
[52] U.S. Cl. ........................................ 602/19; 2/338
[58] Field of Search ................ 128/876; 602/19, 47; 2/338, 311, 312, DIG. 1

[56] References Cited

U.S. PATENT DOCUMENTS

| | | | |
|---|---|---|---|
| 818,031 | 4/1906 | Kislik | 2/338 |
| 1,731,100 | 10/1929 | Herbener | 2/338 |
| 1,950,257 | 3/1934 | Mix | 2/338 |
| 2,632,894 | 3/1953 | Louis | 2/338 |
| 2,687,129 | 8/1954 | Talkish | 602/19 |
| 3,420,230 | 1/1969 | Ballard | 602/19 |
| 3,434,469 | 3/1969 | Swift | 602/19 |
| 3,509,875 | 5/1970 | Richter | 602/19 |
| 5,046,488 | 9/1991 | Schiek | 2/338 |

*Primary Examiner*—Michael A. Brown
*Attorney, Agent, or Firm*—Lowe, Price, LeBlanc & Becker

[57] ABSTRACT

A medical belt consists of a front belt portion and a back belt portion, respectively made of a semi-rigid and half-resilient material. These belt portions, respectively have a number of ventilation and engagement holes formed on almost whole surfaces of them. One of the belt portions has a plurality of hooking pieces and fitting protrusions formed on both ends portions of the belt portion, and the hooking pieces and the fitting protrusions are adapted to engage with the ventilation and engagement holes formed on another belt portion. In operation, an end of the front belt portion and an end of the back belt portion are connected by engaging the hooking pieces and fitting protrusions with the ventilation and engagement holes, then the front belt portion is applied to a belly of a user of the medical belt and the back belt portion is passed to a back of the user and applied to a waist, and finally any ventilation and engagement holes formed an another belt portion are engaged with the hooking pieces and fitting protrusion.

2 Claims, 5 Drawing Sheets

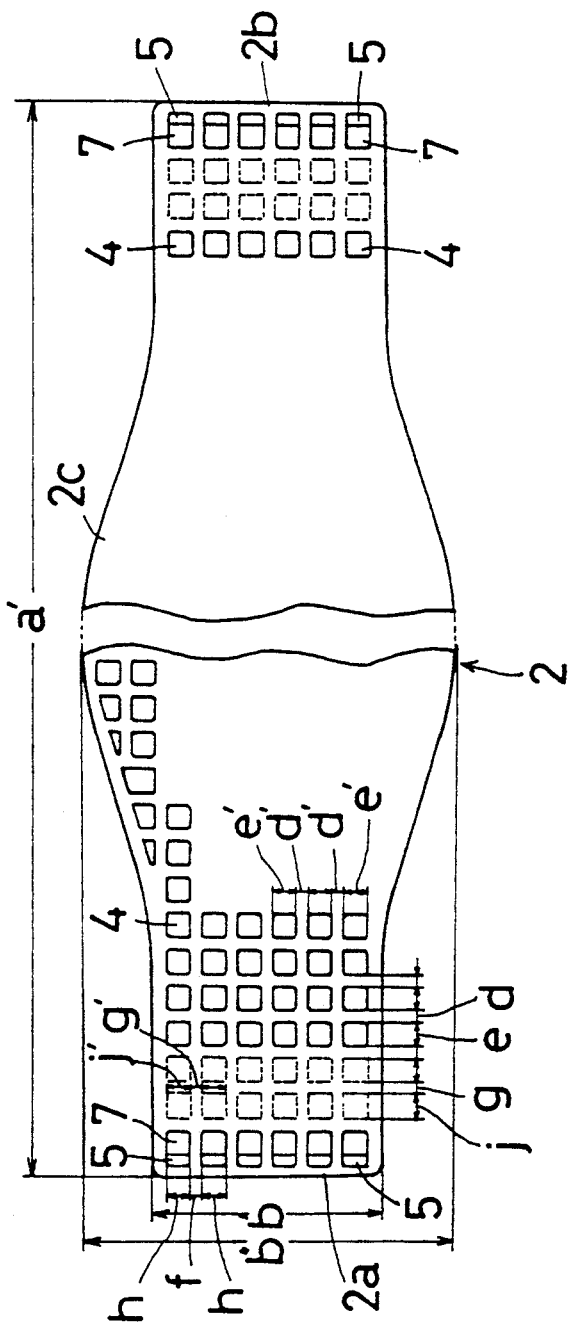
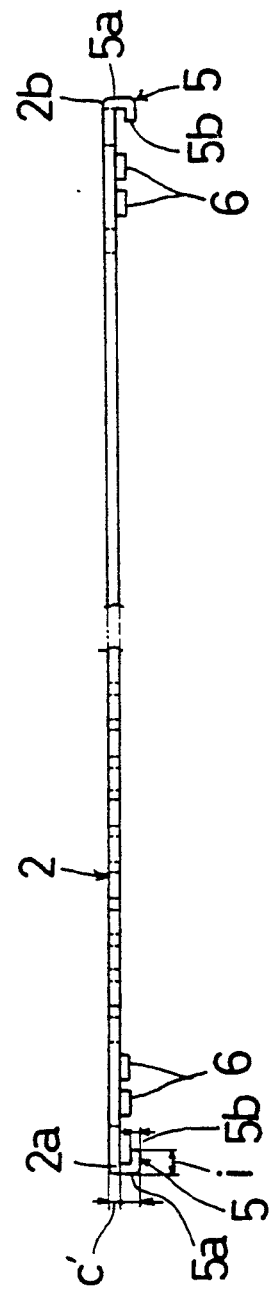

MEDICAL BELT

BACKGROUND OF THE INVENTION

The present invention relates to a medical belt for holding mainly lumbers of human beings in order to alleviate pain in the lumber by reducing a load to be imposed on the lumber or waist.

Conventionally, some medical belts, stays or figure-beauty supports, or belts for shaping waist have been made of rubber in a shape of ring, or leather or plastic material, and they have metal-made-fastening fixtures fixed to the ends of the various belts mention above.

However, such ring-like belts made of rubber have poor ventilation resulting in stuffiness of the body. As a result, the wearer of the belts feel uncomfortable after a long time wearing. According to other inconvenience of the conventional belts, it is impossible to adjust the length or fitness according to the waist size of the wearer or user of the belt, and it is troublesome to put on and take off the belts.

Such belt provided with a fastening fixture fixed to an end portion of the belt has a limitation in its length adjustment and it is impossible to adjust in a wide range of the length. Consequently, it has been necessary to manufacture a number of belts having various sizes.

In addition, in a manufacturing process for the conventional belts, it has been necessary to carry out a step for attaching the fixture to the belt. The step makes the manufacturing process more complicated, and the cost high. Due to an attaching of the fixture to the belt main body, the main body is made weak and the belt is susceptible to be broken for a relative short period of use because the main body of, for example, a plastics made belt is not binded strongly to the metal fixture.

SUMMARY OF THE INVENTION

The present invention has been invented in order to solve the problem above of the conventional belt, in particular of a medical belt.

Accordingly, it is the purpose of the present invention to provide a medical belt enabling to adjust its length in a wide range of various waist sizes of the users, to easily adjust and put on and take off from the users, to make it have good ventilation, and to easily manufacture.

In order to attain the purpose mentioned-above, the medical belt according to the present invention consists of a pair of sash-like front belt portion and back belt portion, both the belt portions have a number of ventilation and engagement holes formed on almost entire surfaces of the belt portions, one of the belt portions has a predetermined number of hooking pieces and fitting protrusions adapted to engage with the ventilation and engagement holes of another belt portion, these hooking pieces and fitting protrusions are integrally formed at both end portions of the one belt portion.

It is preferable to configure the hooking piece in a sectional shape of about E without the middle horizontal bar by both end portions of the back belt portion, pending portions pending at a right angle from the end portions, and engagement portions extending at a right angle toward the inside of the belt portion from the lower ends of the pending portions.

Additionally, it is preferable to arrange the hooking pieces to be formed on rear faces of the ends of the back belt portion in a row along the width direction of the back belt portion with a regular interval.

The fitting protrusions are preferably placed inside of the positions of the hooking pieces in a plurality of rows and arranged along the length direction and the width direction of the belt portion with a regular interval.

Before wearing the medical belt of the present invention, the user engages the hooking pieces on an end side of one of the belt portions with the ventilation and engagement holes on an end side of another belt portion, making a long strip-like sash. Then, the front belt portion is applied to a belly of the user, the back belt portion is passed round the back to the waist, and finally the hooking pieces formed on another end portion are engaged with the ventilation and engagement holes formed on another end portion of respective belt portions.

At this time, the engagement or hooked positions of the hooking pieces and the ventilation and engagement holes are determined according to the particular waist size of the user or wearer.

The hooking pieces are placed on the edges of the belt portions and the fitting protrusions are placed inside of the positions of the hooking pieces, so the hooking pieces are engaged with the particular ventilation and engagement holes placed inside of the edge of the different belt portion, not engaged with the ventilation and engagement holes placed at the edge of the different belt portion, and simultaneously the fitting protrusions above are fitted to the ventilation and engagement holes correspondingly placed on the end portion of the different or another belt portion.

In operation of the medical belt of the present invention, the hooking pieces are slanted before inserting into the ventilation and engagement holes, respectively formed on the front and the back belt portions, then both belt portions are made in parallel or overlapped with each other, and finally the hooking pieces and the fitting protrusions are engaged with and fitted into the ventilation and engagement holes.

Because the front belt portion and the back belt portion of the medical belt has a little resiliency, when the medical belt is worn by the user, they are pulled and firmly contacted to and hold surely the lumber.

It is convenient that the number of ventilation and engagement holes formed on almost entire surfaces of the front and the back belt portions so as to penetrate through the thickness of the belt portion, so that the user can enjoy comfortable ventilation when the medical belt is worn. In addition, it is possible to adjust the pulling or fitness strength of the medical belt worn around the waist of the user in a wide range.

BRIEF DESCRIPTION OF THE DRAWINGS

FIG. 6 is a plan view of the back belt portion of the embodiment shown in FIG. 1;

FIG. 7 is a side elevation of the back belt portion of the embodiment shown in FIG. 1.

EMBODIMENT

An embodiment of the medical belt according to the present invention will be explained with reference to the accompanying drawings.

Figure 1:
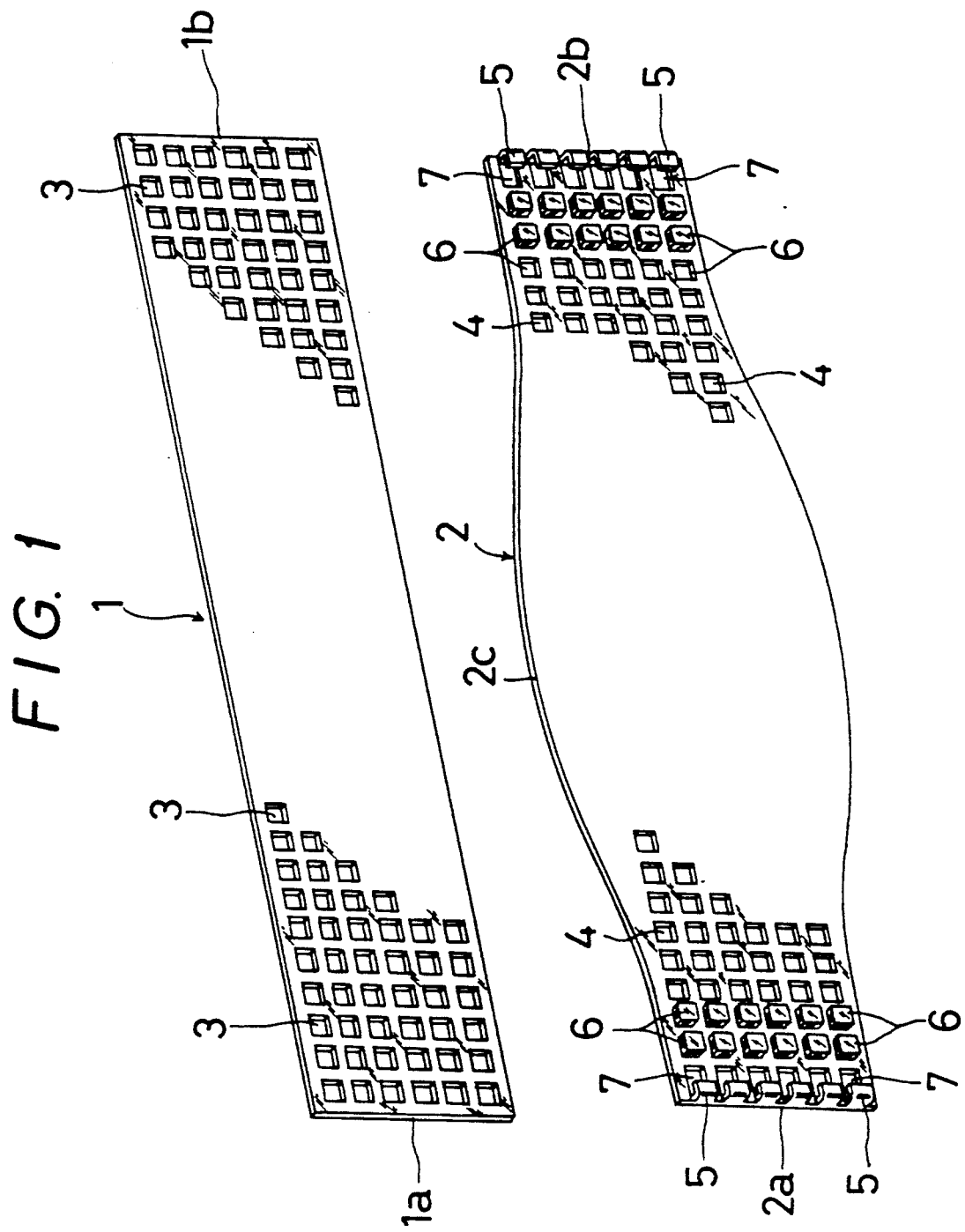
FIG. 1 is a perspective view depicting separately a front belt portion and a back belt portion of the medical belt according to the present invention.

It is noted that as shown apparently in FIG. 1 the medical belt according to the present invention consists of a front belt portion 1 and a back belt portion 2.

The front and back belt portions are made of a half- or semi-rigid type plastics material having a little resiliency or some rubber and leather having characteristics of semi-rigid and small resiliency. These belt portions are made in the shape of strip or sash or band, and have a number of ventilation and engagement holes 3 and 4. The holes are arranged over almost whole surfaces of the front belt portion and the back belt portion, and penetrate through the whole thickness of the portions of the belt according to the present invention. Seeing down the holes, they have a shape of square.

In detail, both of the front belt portion 1 and the back belt portion 2, respectively have generally the same length a and a', and the same thickness c and c'. On the contrary, it is apparent that the front belt portion 1 has a uniform width from its end 1a to another end 1b, and the back belt portion 2 has both end portions 2a and 2b of relatively narrow and a wide central portion 2c expanding outward from a top side and a bottom side of the back belt portion 2 symmetrically in a shape of arc. Such wide configuration of the back belt is convenient to fix or settle, for example, lumbers and the like effectively.

According to the embodiment of the front belt portion 1 and the back belt portion 2, they have lengths a, a' of about 594 mm, and thickness c, c' of about 3 mm. A width b of the front belt portion 1 is identical with the width b' of both end portions 2a, 2b of the back belt portion 2, and these widths b and b' are set for about 65 mm and the width b" of the wide central portion 2c of the back belt portion 2 are set for about 105 mm.

The back belt portion 2 as shown in FIG. 1 has a plurality of hooking pieces 5, respectively formed on a rear face of the end portions 2a, 2b of the back belt portion 2, and a plurality of fitting protrusions 6. The hooking pieces 5 are formed on both edges of the end portions 2a and 2b of the back belt portion 2 so as to engage detachably with the ventilation engagement holes 3 of the front belt portion 1. The fitting protrusions 6 are adapted to fit detachably into the ventilation engagement holes 3 formed on the front belt portion 1.

Figure 4:
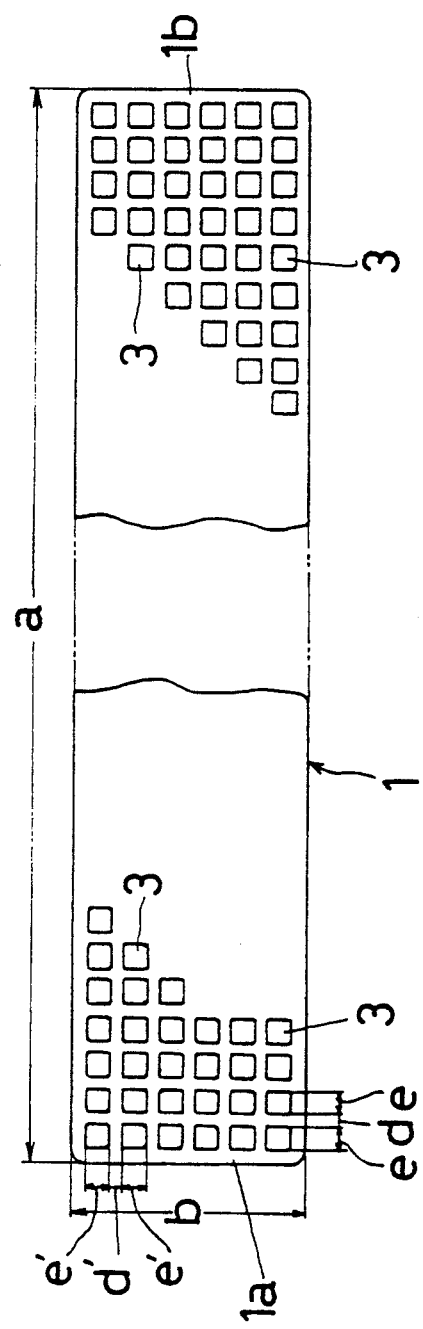
FIG. 4 is a plan view showing the front belt portion of the embodiment shown in FIG. 1.
Figure 5:
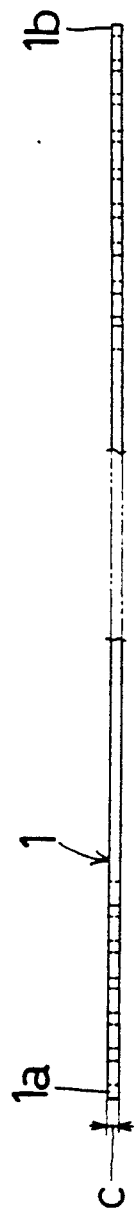
FIG. 5 is a side elevation of the front belt portion of the embodiment shown in FIG. 1.
Figure 8:
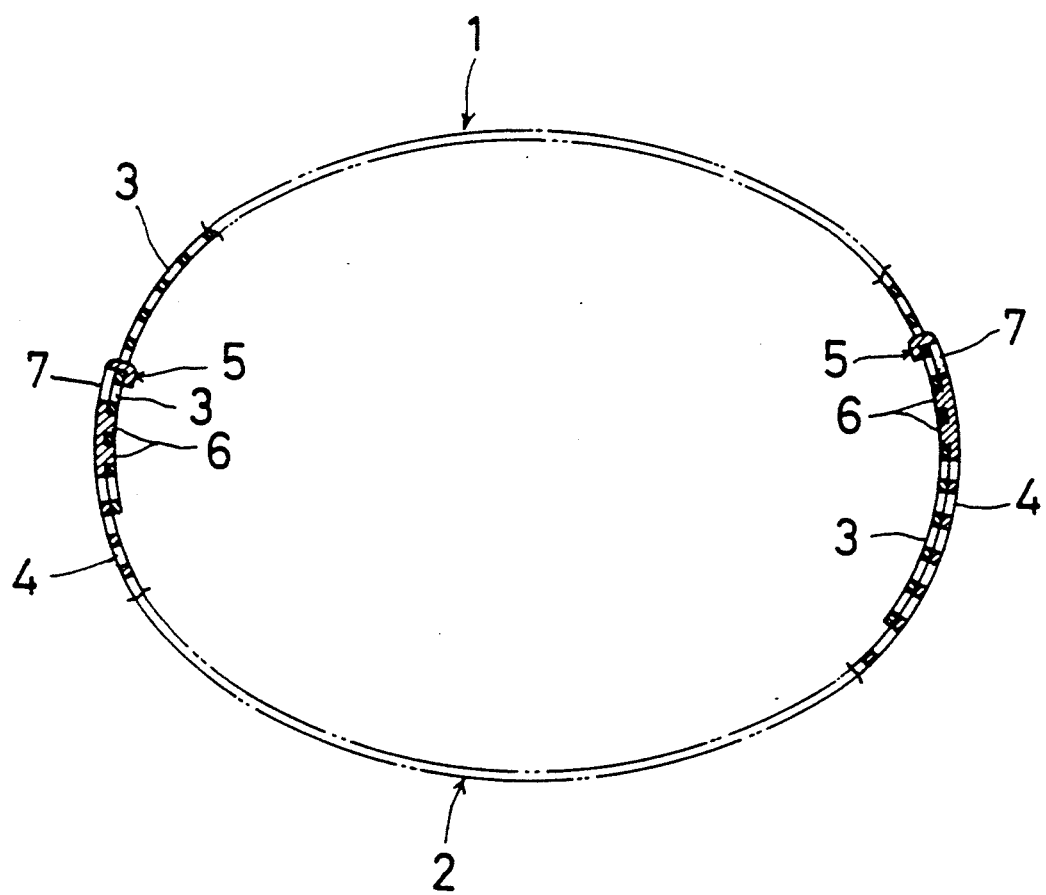
FIG. 8 is a partially sectioned plan view depicting a usage condition of the belt shown in FIG. 1 according to the present invention.

It is apparent from FIG. 4 to FIG. 6 that these ventilation and engagement holes 3 and 4, respectively formed on the front and the back belt portions 1 and 2 are placed in rows along their length direction and width direction of these belt portions 1 and 2 at regular intervals d and d'. According to the shown embodiment of the present invention, the ventilation and engagement holes 3 and 4 have a regular square in their plan viewings, and these sizes e and e' of the square have been set for about 6.8 mm and are adapted to have intervals of about 3.2 mm.

In detail the hooking pieces 5 are arranged in a row at the edges of both the end portion 2a and 2b of the back belt portion 2 with a regular interval f. The fitting protrusions 6, respectively formed on a inner side of a length direction of the back belt portion 2 in two rows along the width direction with regular intervals g and g'. It is of course that one row or three rows of the fitting protrusions 6 may be formed on the back belt portion 2.

As shown in FIG. 7 the hooking pieces 5 respectively have both end portions 2a and 2b of the back belt portion 2, pending portions 5a pending from the end portions 2a and 2b at a right angle, and engagement portions 5b extending from the lower ends of the pending portions 5a horizontally or at a right angle toward the inside of the back belt portion 2. At positions of the back belt portion 2 and facing the engagement portions 5b of the both end portions 2a and 2b, there are holes 7 for trimming dies used in a plastic molding step.

As shown in FIG. 6, the width h and the distance or interval f of the hooking piece 5 are the same as that of the size e' and the distance or interval d' of the ventilation and engagement holes 3 formed in the front belt portion 1: respectively about 6.8 mm and 3.2 mm. And the length i of the engagement portion 5b measured from the end face of the back belt portion 2 is set to about 6.2 mm.

The measurements j, j' along two directions at a right angle of the fitting protrusions 6 are adapted to be a little small than that of the ventilation and engagement holes 3 of the front belt portion 1, as shown in FIG. 6, for example, of about 6.6 mm. Consequently, the distances g and g' between the square ventilation and engagement holes 4 are set to about 3.4 mm which is a little larger than the distances d, d' of the ventilation and engagement holes 3. As a result, in engagement operation of the medical belt according to the present invention, the front belt portion and the back belt portion are effectively and firmly engaged with each other as described below.

Figure 2:
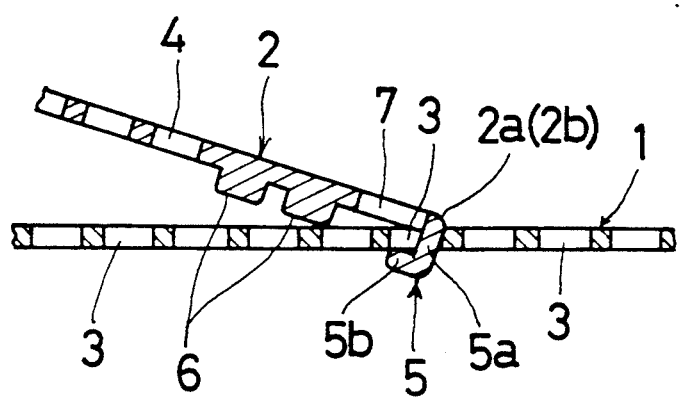
FIG. 2 is a partial section depicting a transit condition of fastening of the front belt portion and the back belt portion according to the embodiment shown in FIG. 1.
Figure 3:
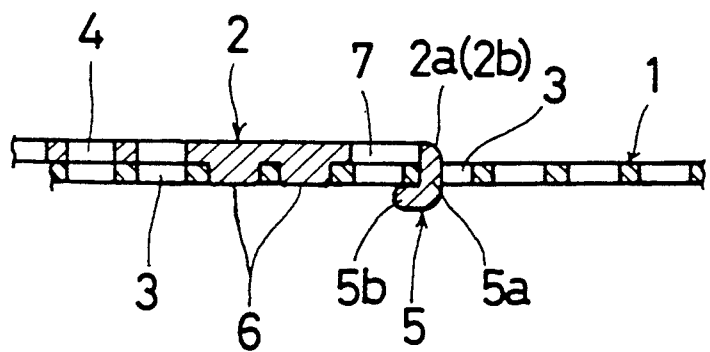
FIG. 3 is a partial section showing a fastened condition of the front belt portion and the back belt portion of the belt shown in FIG. 1 according to the present invention.

First, the hooking piece 5 of the back belt portion 2 is slanted and inserted into the ventilation and engagement hole 3 of the front belt portion 1 as shown in FIG. 2. Then, the back belt portion 2 is compulsorily attached on the front belt portion 1 in parallel relation by hands and the former is overlapped with the latter. As a result, the engagement portion 5b of the hooking piece 5 is engaged with the bottom edge of any ventilation and engagement hole 3 formed on the front belt portion 1, and the fitting protrusions 6 and 6 are forcibly fitted into another ventilation and engagement holes 3 and 3 of the front belt portion 1. An opposite manual operation of the medical belt can sequentially disengage the hooking pieces 5 and the fitting protrusions 6 from the ventilation and engagement holes 3.

According to the embodiment described above of the present invention, the hooking pieces 5 and the fitting protrusions 6 are formed on the back belt portion 2. On the contrary, it is possible to form these hooking pieces 5 and the fitting protrusions 6 on the front belt portion 1.

Because the medical belt of the present invention has the construction mentioned above, the front belt portion 1 can be fastened to the back belt portion 2 through a number of the ventilation and engagement holes 3 provided on the whole surface of one of the belt portions and the hooking pieces 5 and fitting protrusions 6, respectively formed on the other belt portion, which are engaged with and fitted into each other. Accordingly, it is possible to adjust the length of the medical belt according to various waist sizes of the wearers in a wide range. It is called a free size type medical belt. Respective front belt portion 1 and back belt portion 2 can be formed in a unit and they are easily manufactured at a low cost.

In addition, the front and the back belt portions 1 and 2 are made of semi-rigid material having a little resiliency or some pulling force, so that the medical belt can be firmly applied to the waist portion of the human being body and the lumber and its surrounding portion are effectively settled. Additionally, a number of the ventilation and engagement holes 3 and 4 improves ventilation of the medical belt, so bad feeling such as being stuffy of the medical belt is not felt even when it is worn for a long time. The medical belt of the present invention can be easily washed and the wearer or user can enjoy a clean and sanitary belt, and it is dried conveniently in a short time.

It is noted additionally that the fitting protrusions 6 and the hooking pieces 5 formed on the surface of one of the belt portions are engaged with the ventilation and engagement holes 3 formed on another belt portion in the length direction of the medical belt and two directions right angled to the length direction, so that the engagement and fastening strength of the medical belt becomes large. In addition, the hooking pieces 5 formed on one of the belt portions are engaged with the ventilation and engagement holes of another belt portion after the former is inserted and disengaged at a slant into and from the corresponding ventilation and engagement holes. Such manual engagement and disengagement operations between the hooking pieces 5 and the corresponding fitting protrusions 6 are carried out by a single pushing or pulling. It is apparent that the medical belt according to the present invention can be used to other purposes such as a shaping of body, in particular waists and the like.

What is claimed is:

1. A belt arrangement which is adapted to surround a waist or trunk area that has a certain circumference so as to supply support or reduce discomfort to said waist or said trunk area, said belt arrangement consisting of
   (1) two separate belt portions consisting of a front belt portion and a back belt portion, each of said two belt portions having a length which is less than said certain circumference,
   (2) both of said belt portions
       (a) being composed of semi-rigid material of limited resiliency, and
       (b) containing a plurality of holes which provide ventilation,
   (3) a first set of hooking members located adjacent a end of said back belt portion which engage some of said holes in said front belt portion, and a second set of hooking members located adjacent another end of said back belt portion which engage some of said holes in said front belt portion, and
   (4) a first set of protrusions located adjacent the end of said back belt portion inwardly of said first set of hooking members which engage some of said holes in said front belt portion and a second set of protrusions located adjacent another end of said back belt portion inwardly of said second set of hooking members which engage some of said holes in said front belt portion whereby the interlocking of said hooking members and protrusions with said holes in said two belt portions forms a unitary circumferential belt arrangement surrounding said waist or trunk area.

2. A belt arrangement which is adapted to surround a waist or trunk area that has a certain circumference so as to supply support or reduce discomfort to said waist or said trunk area, said belt arrangement consisting of
   (1) two separate belt portions consisting of a front belt portion and a back belt portion, each of said two belt portions having a length which is less than said certain circumference,
   (2) both of said belt portions
       (a) being composed of semi-rigid material of limited resiliency, and
       (b) containing a plurality of holes which provide ventilation,
   (3) a first set of hooking members located a end of said front belt portion which engage some of said holes in said back belt portion, and a second set of hooking members located adjacent another end of said front belt portion which engage some of said holes in said back belt portion, and
   (4) a first set of protrusions located adjacent the end of said front belt portion inwardly of said first set of hooking members which engage some of said holes in said back belt portion and a second set of protrusions located adjacent another end of said front belt portion inwardly of said second set of hooking members which engage some of said holes in said back belt portion whereby the interlocking of said hooking members and protrusions with said holes in said two belt portions forms a unitary circumferential belt arrangement surrounding said waist or trunk area.

* * * * *